(12) United States Patent
Norris (10) Patent No.: US 10,031,071 B2
(45) Date of Patent: Jul. 24, 2018

(54) TEXTURE ANALYSIS OF A COATED SURFACE USING KEPLER'S PLANETARY MOTION LAWS

(71) Applicant: PPG Industries Ohio, Inc., Cleveland, OH (US)

(72) Inventor: Alison M. Norris, Avon, OH (US)

(73) Assignee: PPG Industries Ohio, Inc., Cleveland, OH (US)

( * ) Notice: Subject to any disclaimer, the term of this patent is extended or adjusted under 35 U.S.C. 154(b) by 612 days.

(21) Appl. No.: 14/535,399

(22) Filed: Nov. 7, 2014

(65) Prior Publication Data

US 2015/0134269 A1   May 14, 2015

Related U.S. Application Data

(60) Provisional application No. 61/901,503, filed on Nov. 8, 2013.

(51) Int. Cl.
| | | |
|---|---|---|
| *G01N 31/00* | (2006.01) | |
| *G01N 21/25* | (2006.01) | |
| *G01N 21/55* | (2014.01) | |
| *G01N 33/32* | (2006.01) | |
| *G01J 3/50* | (2006.01) | |
| *G01J 3/46* | (2006.01) | |

(52) U.S. Cl.
CPC ............ *G01N 21/251* (2013.01); *G01J 3/463* (2013.01); *G01J 3/504* (2013.01); *G01N 21/55* (2013.01); *G01N 33/32* (2013.01); *G01J 2003/467* (2013.01); *G01N 2201/12* (2013.01)

(58) Field of Classification Search
None
See application file for complete search history.

(56) References Cited

U.S. PATENT DOCUMENTS

| | | |
|---|---|---|
| 3,927,944 A | 12/1975 | Iwahashi |
| 3,972,617 A | 8/1976 | Shibata |
| 4,092,069 A | 5/1978 | Fukuda |

(Continued)

FOREIGN PATENT DOCUMENTS

| | | |
|---|---|---|
| CN | 1635957 A | 7/2005 |
| CN | 1797420 | 7/2006 |

(Continued)

OTHER PUBLICATIONS

Takagi A et al: "Prediction of spectral reflectance factor distribution of color-shift paint finishes", Color Research & Application, John Wiley & Sons, Inc, US, vol. 32, No. 5, Oct. 1, 2007, pp. 378-387, XP002604927, ISSN: 0361-2317, abstract, p. 380, right-hand column—p. 383, p. 386, left-hand column.

(Continued)

*Primary Examiner* — Calvin Choi
(74) *Attorney, Agent, or Firm* — Christine W. Trebilcock (57) ABSTRACT

A method that includes obtaining, using a processor, reflectance data from a target coating and calculating, using the processor, virtual color response data using one of at least one Kepler's laws of planetary motion equation and at least one derivation of at least one Kepler's laws of planetary motion equation. The method also includes generating, using the processor, a coating formulation that is the same or substantially similar in appearance to the target coating.

20 Claims, 6 Drawing Sheets

(56) References Cited

U.S. PATENT DOCUMENTS

| | | | |
|---|---|---|---|
| 4,164,374 A | 8/1979 | Lambe | |
| 4,344,142 A | 8/1982 | Diehr, II | |
| 4,479,718 A | 10/1984 | Alman | |
| 4,711,580 A | 12/1987 | Venable | |
| 5,231,472 A | 7/1993 | Marcus | |
| 5,319,437 A * | 6/1994 | Van Aken | G01J 3/02 356/326 |
| 5,590,251 A | 12/1996 | Takagi | |
| 5,612,928 A | 3/1997 | Haley | |
| 5,926,262 A | 7/1999 | Jung | |
| 6,166,841 A | 12/2000 | Pringle | |
| 6,249,751 B1 | 6/2001 | Asaba et al. | |
| 6,449,384 B2 | 9/2002 | Di Venuto | |
| 6,539,325 B1 | 3/2003 | Numata et al. | |
| 6,794,669 B2 | 9/2004 | Chelvayohan et al. | |
| 7,809,155 B2 | 10/2010 | Nestares | |
| 7,944,561 B2 | 5/2011 | Nisper et al. | |
| 8,345,252 B2 | 1/2013 | Nisper et al. | |
| 8,606,731 B2 | 12/2013 | Fujieda et al. | |
| 8,879,066 B2 | 11/2014 | Norris | |
| 9,482,657 B2 | 11/2016 | Bell | |
| 2003/0208345 A1 | 11/2003 | O'Neill | |
| 2005/0128484 A1* | 6/2005 | Rodrigues | G06T 11/001 356/402 |
| 2005/0169518 A1 | 8/2005 | Boston et al. | |
| 2005/0206383 A1* | 9/2005 | Park | G01R 33/30 324/321 |
| 2006/0030060 A1 | 2/2006 | Noguchi et al. | |
| 2006/0045831 A1* | 3/2006 | Galembeck | C01B 25/36 423/311 |
| 2006/0245632 A1 | 11/2006 | Nisper et al. | |
| 2007/0019887 A1 | 1/2007 | Nestares | |
| 2007/0172113 A1 | 7/2007 | Sai et al. | |
| 2007/0200337 A1 | 8/2007 | Johnson et al. | |
| 2007/0226158 A1 | 9/2007 | Woronow | |
| 2007/0250273 A1 | 10/2007 | De Haas | |
| 2008/0177586 A1 | 7/2008 | Jamjoom | |
| 2008/0235224 A1 | 9/2008 | Rodrigues et al. | |
| 2008/0278723 A1 | 11/2008 | Merchak | |
| 2009/0015835 A1 | 1/2009 | Balakrishnen et al. | |
| 2009/0157212 A1 | 6/2009 | McClanahan | |
| 2009/0190839 A1 | 7/2009 | Higgins | |
| 2009/0213120 A1 | 8/2009 | Nisper et al. | |
| 2009/0292520 A1 | 11/2009 | Nwankpa | |
| 2010/0048242 A1 | 2/2010 | Rhoads | |
| 2010/0228511 A1 | 9/2010 | Chin et al. | |
| 2011/0282613 A1 | 11/2011 | Skinner | |
| 2012/0225190 A1 | 9/2012 | Steenhoek | |
| 2012/0243797 A1 | 9/2012 | Di Venuto | |
| 2012/0303376 A1 | 11/2012 | Shishido | |
| 2013/0244197 A1 | 9/2013 | Tijoe | |
| 2014/0078293 A1 | 3/2014 | Beymore | |
| 2014/0118936 A1 | 5/2014 | Merlet et al. | |
| 2014/0242271 A1 | 8/2014 | Prakash et al. | |
| 2014/0250109 A1 | 9/2014 | Wang | |
| 2014/0278251 A1 | 9/2014 | Norris | |
| 2014/0278253 A1* | 9/2014 | Beymore | G06N 7/005 702/189 |
| 2014/0278254 A1 | 9/2014 | Beymore | |
| 2015/0023054 A1 | 1/2015 | Goda et al. | |
| 2015/0127269 A1 | 5/2015 | Bell | |
| 2015/0134269 A1 | 5/2015 | Norris | |
| 2015/0134299 A1 | 5/2015 | Norris | |
| 2015/0134300 A1 | 5/2015 | Norris | |

FOREIGN PATENT DOCUMENTS

| | | |
|---|---|---|
| CN | 101184986 | 5/2008 |
| CN | 101646929 | 2/2010 |
| CN | 101784871 | 7/2010 |
| CN | 102549545 | 7/2012 |
| JP | 2002236850 | 8/2002 |
| JP | 2007218895 | 8/2007 |
| KR | 20100102147 | 9/2010 |
| TW | 200608310 | 3/2006 |
| TW | 200821602 | 5/2008 |
| TW | 200834273 | 8/2008 |
| TW | 201339652 A | 10/2013 |
| WO | 03063719 A1 | 8/2003 |
| WO | 2006096521 | 9/2006 |
| WO | 2006112864 | 10/2006 |
| WO | 200709402 | 1/2009 |
| WO | 2013049792 A1 | 4/2013 |
| WO | 2013116192 | 8/2013 |
| WO | 2014150337 | 9/2014 |

OTHER PUBLICATIONS

Anonymous, "Chapter 1.3.5.17. Detection of Outliers", NIST/SEMATECH e-Handbook of Statistical Methods, Jan. 1, 2012, XP055162021.

Paravina et al, "Evaluation of blending effect of composites related to restoration size", Dental Materials, Elsevier, Amsterdam, NL, vol. 22, No. 4, Apr. 1, 2006, pp. 299-307, XP027943381, ISSN: 0109-5641 table 2.

Beymore, Paul M., U.S. Appl. No. 14/121,869, "Pigment Identification of Complex Coating Mixtures with Sparkle Color", filed Oct. 28, 2014.

Non-Final Office Action in U.S. Appl. No. 14/535,380 dated Apr. 12, 2017.

Office Action in application No. 201480070100.X dated Feb. 27, 2017.

Final Office Action for U.S. Appl. No. 14/535,380 dated Oct. 27, 2017.

Final Office Action for U.S. Appl. No. 14/535,372 dated Oct. 6, 2017.

Non-Final Office Action for U.S. Appl. No. 14/535,372 dated Jun. 20, 2017.

Non-Final Office Action for U.S. Appl. No. 13/832,116 dated Mar. 5, 2014.

"Kuncheva, Ludmila I., James C. Bezdek, and Robert PW Duin. ""Decision templates for multiple classifier fusion: an experimental comparison."" Patternrecognition 34.2. 2001."

Korean Office Action in application No. 201507025129 dated Jun. 21, 2016.

Final Office Action for U.S. Appl. No. 13/832,554 dated Apr. 20, 2016.

I. Lissner, U. Philipp: "Upgrading Color-Difference Formulas", Journal of the Optical Society of America, vol. 27 No. 7, Jun. 11, 2010 (Jun. 11, 2010), pp. 1620-1629, XP055152562, DOI: 10,1364/JOSAA.27.001620 Sections 1 and 2.A.

D. Puig, M.A. Garcia, J. Melendez: "Application-Independent feature selection for texture classification", Pattern Recognition, vol. 43, No. 10, May 10, 2010 (May 10, 2010) pp. 3182-3297, XP027095420, DOI: 10. 1016/j.patcog.2010.05.005 abstract and section 3.

J.H. Xin, S. Shao, K.F.-L. Chung: "Colour-appearance modelling using feedforward networks with Bayesian regularization method-part 1: forward model", Color Research & Application, vol. 25, No. 6, Oct. 13, 2000, pp. 424-434, XP055152560, DOI: 10.1002/1520-6378(200012)25:6<424:AID-COL7>3.0.CO;2-Q.

E. Kirchner: "Appearance and measurement modeling an drendering of the visual texture of automotive paints", Detroit Color Council, Mar. 13, 2013, XP055153196, Retrieved from the Internet: URL: http://www.detroitcc.org/files/2013March14b.pdf, [retrieved on Apr. 3, 2013] Models for predicting Texture.

E.J.J. Kirchner, J. Ravi: "Setting tolerances on color and texture for automotive coatings", Color Research & Application, vol. 39, No. 1, Jul. 25, 2012 pp. 88-98, XP055152561, DOI:10.1002/col.21767.

PPG Automotive Refinish: "RapidMatch™ X-5:guida utente", Pittsburgh Plate Glass (PPG) Industries, 2013, XP055153237, retrieved from the Internet: URL:http://it.nexaautocolor.com/media/213903/rapidmatch_v1-2012_email_version.pdf [retrieved on Sep. 22, 2014].

Non-Final Office Action for application No. 13832554 dated Sep. 23, 2015.

(56) References Cited

OTHER PUBLICATIONS

Kokla, Vassiliki et al., A Bayesian decision model for watercolour analysis, Proc. of SPIE, 2007, vol. 6618, pp. 66180S-1-66180S-9.
Korean Office Action for application No. 2015/7025129 dated Dec. 29, 2016.
Chinese Office Action for application No. 201480015524.6 dated Dec. 26, 2016.
Final Office Action for application No. 13832554 dated Sep. 6, 2017.
Non-Final Office Action for application No. 13832554 dated May 2, 2017.
Alice vs CLS Bank (Supreme Court Decision) (2013).
Notice of Allowance from U.S. Appl. No. 13/835,675 dated Nov. 1, 2016.
Non-Final Office Action from U.S. Appl. No. 13/835,675 dated Sep. 16, 2015.
Taiwan Office Action for application No. 103109480 dated Sep. 17, 2015.
Taiwan Office Action for application No. 103109480 completed on Jul. 17, 2016.
Korean Office Action in application No. 2015-7025121 dated Jul. 25, 2016.
International Search Report for application No. PCT/US2014/022983 dated Nov. 28, 2014.
Korean Office Action in application No. 2015-7025121 dated Jan. 31, 2017.
Chinese Office Action in application No. 201480015523.1 dated Feb. 7, 2017.
Non-Final Office Action in U.S. Appl. No. 13/835,675 dated May 2, 2017.
Final Office Action for U.S. Appl. No. 13/835,675 dated Dec. 12, 2017.
Non-Final Office Action for U.S. Appl. No. 13/832,554 dated Dec. 12, 2017.
Non-Final Office Action for U.S. Appl. No. 14/535,372 dated Feb. 15, 2018.
Li Sun and Richard M. Crooks in Molecular Interactions between Organized, Surface Confided Monolayers and Vapor-Phase Probe Molecules. 5. Acid-Base Interactions, 1993 American Chemical Society, pp. 1775-1780.

* cited by examiner

TEXTURE ANALYSIS OF A COATED SURFACE USING KEPLER'S PLANETARY MOTION LAWS

CROSS REFERENCE TO RELATED APPLICATION

The present application claims priority to U.S. Provisional Application No. 61/901,503, filed on Nov. 8, 2013.

FIELD OF THE INVENTION

Embodiments of the present invention generally relate to the use of Kepler's laws of planetary motion to relate spectral reflectances or colorimetric information from spectrophotometric angles and/or incident light sources to identify the proper pigment(s) to match both the texture and/or gonioapparent effect(s) occurring within an unknown target coating.

BACKGROUND OF THE INVENTION

In a standard portable spectrophotometer, the incident light is generally set at an angle of forty-five (45) degrees from normal. The resulting spectral reflectances that can be gathered are generally in the same plane as the incident light and are on either side of the specular angle (equal and opposite angle to the incident light) as well as nearer to the incident light source itself.

New portable spectrophotometric devices offer a vast multitude of angular color response (spectral reflectance) data. Besides the addition of several new angles, including azimuthal, or out-of-plane, angles, many instruments also offer additional light sources with different geometries from standard. By way of example, the incident light source of a second illuminator may be located at fifteen (15) degrees from normal. The plurality of combinations of incident light and angular response can be both too little and too much information to be handled at one time.

Thus, there is a need for systems and methods that may be used to evaluate all of the data and specific combinations of data from a spectrophotometer.

SUMMARY OF THE INVENTION

In a first aspect, embodiments of the invention provide a computer implemented method. The method includes obtaining, using a processor, reflectance data from a target coating and calculating, using the processor, virtual color response data using one of at least one Kepler's laws of planetary motion equation and at least one derivation of at least one Kepler's laws of planetary motion equation. The method also includes generating, using the processor, a coating formulation that is the same or substantially similar in appearance to the target coating.

In another aspect, embodiments of the invention are directed to a system. The system includes a database and a processor in communication with the database. The processor is programmed to obtain reflectance data from a target coating, calculate virtual color response data using one of at least one Kepler's laws of planetary motion equation and at least one derivation of at least one Kepler's laws of planetary motion equation, and generate a coating formulation that is the same or substantially similar in appearance to the target coating.

In another aspect, embodiments of the invention provide an apparatus. The apparatus includes means for obtaining reflectance data from a target coating and means for calculating virtual color response data using one of at least one Kepler's laws of planetary motion equation and at least one derivation of at least one Kepler's laws of planetary motion equation. The apparatus also includes means for generating a coating formulation that is the same or substantially similar in appearance to the target coating.

In a further aspect, embodiments of the invention provide a non-transitory computer readable medium including software for causing a processor to: obtain reflectance data from a target coating; calculate virtual color response data using one of at least one Kepler's laws of planetary motion equation and at least one derivation of at least one Kepler's laws of planetary motion equation; and generate a coating formulation that is the same or substantially similar in appearance to the target coating.

DETAILED DESCRIPTION OF THE INVENTION

While the description herein generally refers to paint, it should be understood that the devices, systems and methods apply to other types of coatings, including stain and industrial coatings. The described embodiments of the invention should not be considered as limiting. A method consistent with the present invention may be practiced in a variety of fields such as the matching and/or coordination of apparel and fashion products.

Embodiments of the invention may be used with or incorporated in a computer system that may be a standalone unit or include one or more remote terminals or devices in communication with a central computer via a network such as, for example, the Internet or an intranet. As such, the computer or "processor" and related components described herein may be a portion of a local computer system or a remote computer or an on-line system or combinations thereof. The database and software described herein may be stored in computer internal memory or in a non-transitory computer readable medium.

Embodiments of the invention are directed generally to spectral and/or colorimetric analysis of coatings, and more particularly, but not by way of limitation, to devices, methods and systems for predicting and formulating a complex coating mixture containing metallic, pearlescent, and/or special effect pigments.

In various embodiments, the present invention generally relates to a method and apparatus for identifying physical property attributes of cured complex coating (e.g., paint) mixtures using Kepler's laws of planetary motion data that are calculated, using a processor, based on the spectral reflectance and colorimetric response from a spectrophotometer.

In various embodiments, the purpose of using Kepler's laws of planetary motion methodology is multi-fold. First, in order to use all available angles within a given system, Kepler's laws of planetary motion may be used to create an alternate bi-directional reflectance distribution function ("BRDF")-type analysis. This type of analysis does not exclude any angles, rather using all angles to create a hemispherical "map" or "fingerprint" of a particular texture or pigment type, whether gonioapparent or not. This methodology may be used to pseudo-interpolate angular responses that are not physically captured by the instrument at hand. Second, Kepler's laws of planetary motion may be used to evaluate only specific combinations of angles in order to achieve purposeful manipulations. Similarly, this includes the exclusion of specific singular angles or combinations of angles when a particular texture or effect is being sought after as included or not included in a target coating. Third, Kepler's laws of planetary motion may be used to accommodate for and correct the potential assumption that the received spectral reflectance values are incorrect in some way. Some potential reasons for irregularity or abnormality of the spectral reflectance data, even if minor, may include incident light angle location, incident light fluctuation, aperture size, target coating surface non-uniformity, etc.

Figure 1:
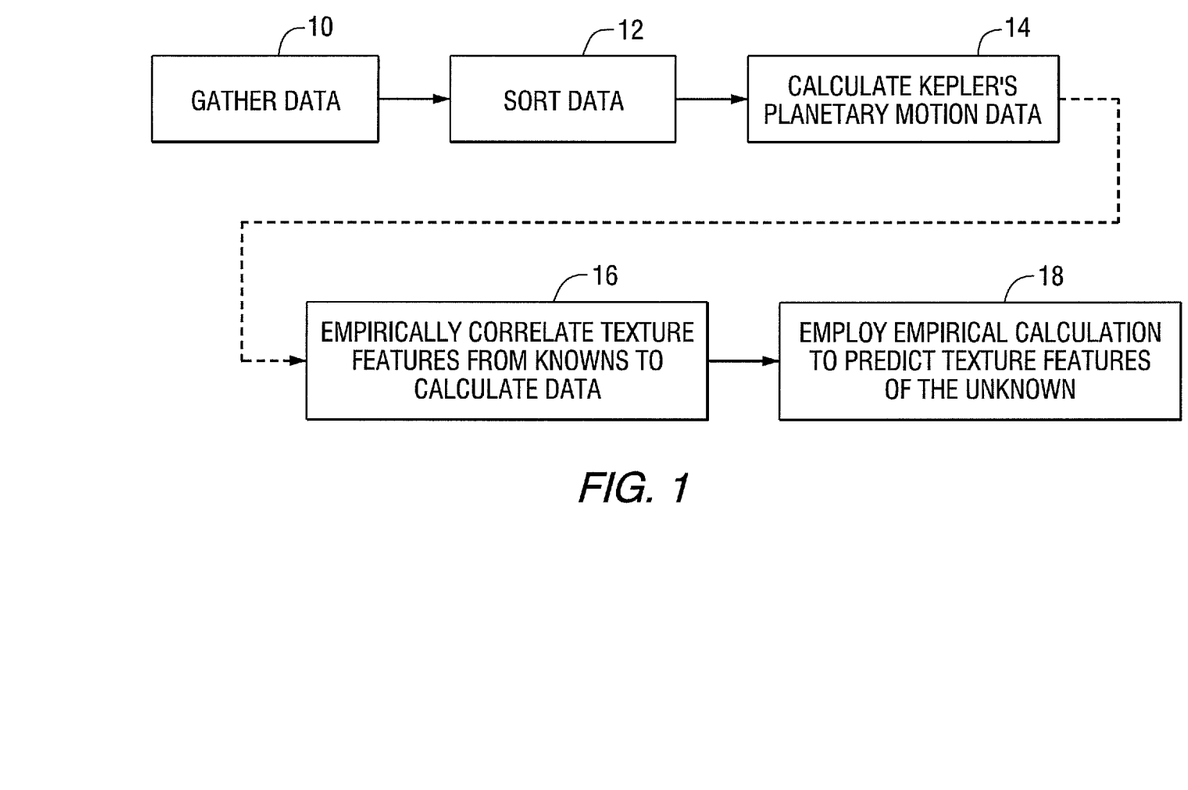
FIG. 1 illustrates an embodiment of a process that calculates a formula for a target complex coating.
Figure 2:
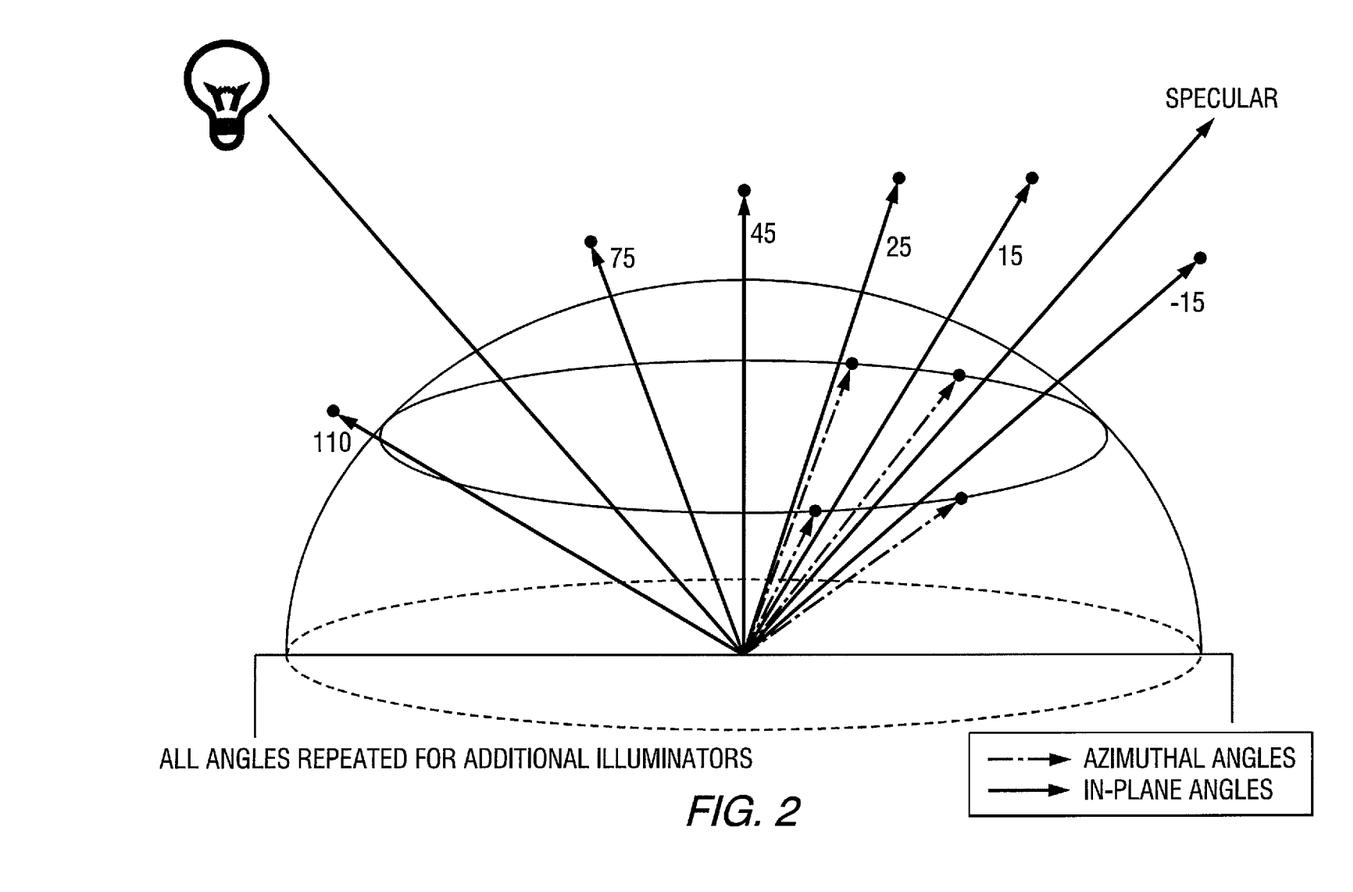
FIG. 2 illustrates a "standard view" of in-plane and out-of-plane angles in a commercially available hand-held spectrophotometer.
Figure 3:
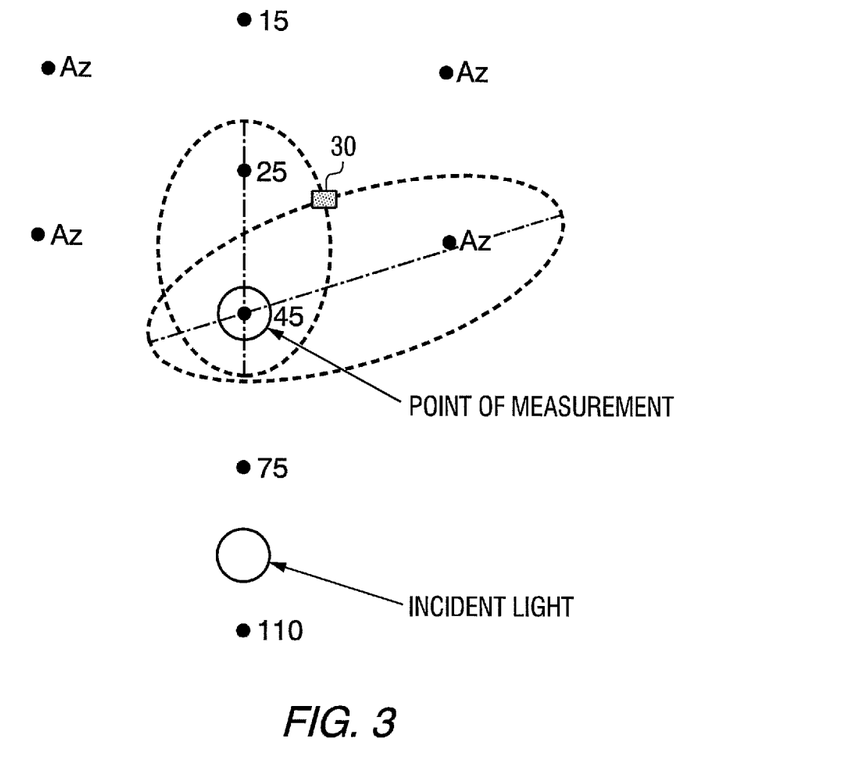
FIGS. 3 and 4 illustrate examples of "top down views" of how multiple angles and light sources may be envisioned using elliptical orbits.
Figure 4:
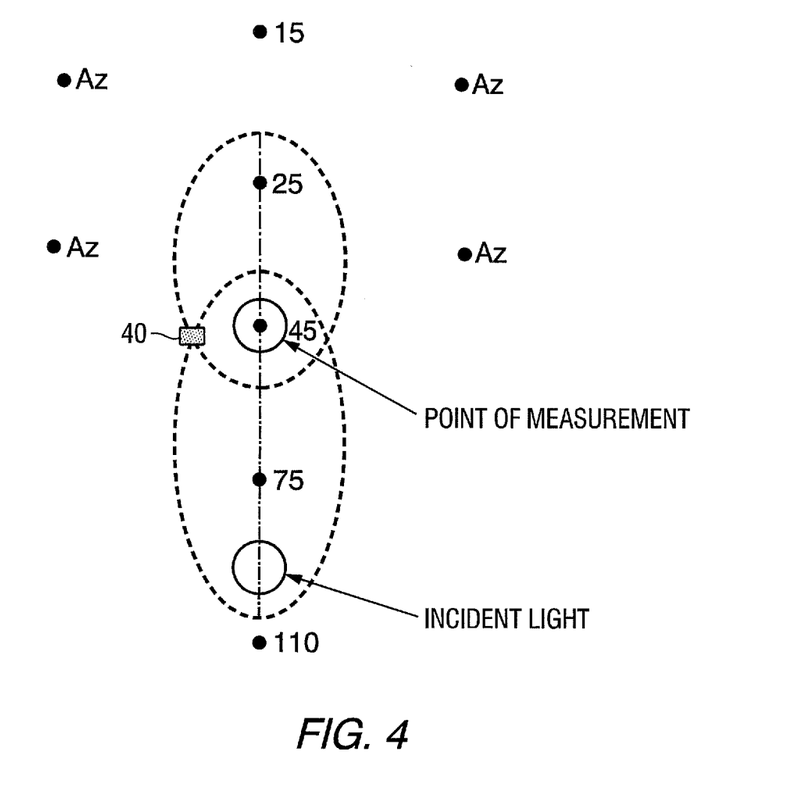

FIG. 1 illustrates an embodiment of a process that calculates a formula for a target complex coating. At step 10, data is gathered from, for example, a spectrophotometer and, at step 12, the data are sorted based on a secondary array of associated information. At step 14, Kepler's laws of planetary motion data is calculated. In various embodiments, the way that individual reflectances or colorimetric information at specific physical angular ports, or angles in conjunction with the incident light angle, will act as foci in an ellipse based on the physical layout of, for example, a portable spectrophotometer may be shown. FIG. 2 illustrates a "standard view" of in-plane and out-of-plane angles in a commercially available spectrophotometer. FIGS. 3 and 4 illustrate examples of "top down views" of how multiple angles and light sources may be envisioned using elliptical orbits where measured angular responses act at the foci of the ellipse. In FIGS. 3 and 4, the squares 30 and 40 indicate an example of a point where the paths cross, which may be a "virtual" color response, meaning that no physical data has been captured at the specific location, however the virtual response may be simulated or calculated based on Kepler's laws of planetary motion, as described herein. Elliptical paths of the color data need not necessarily cross in order to create a virtual color response. Additionally, the elliptical orbits of the color data may be conceptualized as the influence of the real, measured angular color data in relation to other data points, both real and virtual, within the spectrophotometric response. Although FIGS. 3 and 4 illustrate examples, in various embodiments a multitude of combinations are capable using the systems and methods described herein.

Kepler's first law of planetary motion states that "the orbit of every planet is an ellipse with the sun at one of the two foci." In various embodiments, an analogous principle is applied to spectral reflectance and/or colorimetric data based on a spectrophotometer by creating an "orbit" for the relation of several angular responses with either the illuminant light source at one focal point and an angular color response at another focal point, or in which two different angular responses are used for the foci of the related ellipse. In the case where the illuminant light is used as one of the foci, it may be assumed at a singular (output) value along with its inherent location within the spectrophotometer. Using polar coordinates, angular responses within the spectrophotometer may be defined. Values may be calculated using the following equation:

$$r = \frac{p}{1 + \varepsilon \cos\theta} \quad \text{Equation (1)}$$

where r and θ are the polar coordinates for the ellipse, p is the semi-latus rectum, and ε is the eccentricity of the ellipse. By solving for any of the variables, different Kepler's first law of planetary motion values may be calculated based on different input data. In the case of wavelength-dependent spectral reflectance values, the calculations may occur individually for each wavelength and integrated at the end-usage point of the data. In various embodiments, if using the polar coordinates directly from the spectrophotometer unit, these may be functions of at least one of: (1) a version of the angle reflected light, which may be dependent upon the incident light angle; (2) an indication of in-plane or out-of-plane as well as location within that plane; and (3) spectral reflectance value or colorimetric value at a particular wavelength.

Kepler's second law of planetary motion states that "a line joining a planet and the Sun sweeps out equal areas during equal intervals of time." In various embodiments, a planet and the Sun may be analogized to coloristic data as an angular response and the illuminant light source, or any combination thereof, including with and without the illuminant light source. Using Kepler's second law, calculations may be completed using color data. The first equation is that for areal velocity, which takes into account the rate of change of the color based on its proximity to the illuminant light source or other chosen focal point. The areal velocity is defined as:

$$\frac{dA}{dt} = \frac{1}{2}r^2\left(\frac{d\theta}{dt}\right) \quad \text{Equation (2)}$$

where A is the area of a triangle with a base of r and height of rdθ, which may be related to color data as the reflectance or colorimetric data (r) at angle θ, and t is the time element, which can be utilized for color data as an element of physical relation to other points of color response, both real and virtual. A second equation from Kepler's second planetary law of motion is the angular velocity equation applied in relation to the areal velocity. The angular velocity is defined as:

$$\theta_{ang} = \frac{d\theta}{dt} \quad \text{Equation (3)}$$

where $\theta_{ang}$ is the angular velocity, and θ and t may be used to as describe the areal velocity. The last equation that will be discussed within Kepler's second law is that of mean motion, which is that of the planet around the sun. In the case of color, this can be analogized as the mean color or mean rate of change of color around the hemisphere of spectrophotometric color response. The mean motion is defined as:

$$n = \frac{2\pi}{P} \qquad \text{Equation (4)}$$

where n is the mean motion and P is the period of the elliptical orbit as described:

$$P = \frac{\pi ab}{0.5r^2 \theta_{ang}} \qquad \text{Equation (5)}$$

where a and b are related to the area of the elliptical orbit (A=πab), and r and $\theta_{ang}$ can be employed as previously described. In various embodiments, by solving for any of the variables, different Kepler's second law of planetary motion values may be calculated based on different input data. Kepler's second law of planetary motion may be used with respect to color to mathematically determine the rate of change of color over the entire visual response spectrum when observing a coating. In the case of wavelength-dependent spectral reflectance values, the calculations may occur individually for each wavelength and integrated at the end-usage point of the data. In various embodiments, if using the polar coordinates directly from a spectrophotometer unit, these may be functions of at least one of: (1) a version of the angle reflected light, which may or may not be dependent upon the incident light angle; (2) an indication of in-plane or out-of-plane as well as location within that plane; and (3) spectral reflectance value or colorimetric value at a particular wavelength.

Kepler's third law of planetary motion states that "the square of the orbital period of a planet is directly proportional to the cube of the semi-major axis of its orbit." In various embodiments, for color data, the planet may be analogized to a real point of color response from a spectrophotometer and its related orbit may be analogized to the virtual color responses achieved where real physical data is not captured within the spectrophotometer. Kepler's third law is expressed as:

$$P^2 \propto a^3 \qquad \text{Equation (6)}$$

where P is the orbital period of the planet and a is the semi-major axis of the orbit, where the "orbit" may be defined for color by the specific related ellipses drawn based on one or multiple real spectrophotometric response captures and/or the illuminant light source. The related proportionality may be defined for individual scenarios and combinations of spectral reflectance and/or colorimetric data for all color cases or for specific identification of texture subgroups, such as aluminums. In various embodiments, by solving for any variable, different Kepler's third law of planetary motion values may be calculated based on different input data. In the case of wavelength-dependent spectral reflectance values, the calculations may occur individually for each wavelength and integrated at the end-usage point of the data. In various embodiments, if using the polar coordinates directly based off of the spectrophotometer unit, these may be functions of at least one of: (1) a version of the angle reflected light, which may or may not be dependent upon the incident light angle; (2) an indication of in-plane or out-of-plane as well as location within that plane; and (3) spectral reflectance value or colorimetric value at a particular wavelength.

While FIGS. 3 and 4 illustrate examples of specific combinations of angles and/or illuminant light sources for consideration with Kepler's laws of planetary motion, in various embodiments any single or multiple combinations of angular data, both real and virtual, may be used with various forms of Kepler's laws. Additionally, other variables or overall calculations or transformations thereof within Kepler's laws of planetary motion may be used in place of or in conjunction with the first, second, and third laws as described herein. Singular, paired, etc. comparisons may provide a sizeable amount of information that can be used to understand texture. In various embodiments, the incident light angle, either from normal or from parallel, may be used within the coordinate definitions of other angular data. This may be useful when using data from multiple incident light angles or when including a comparison of the data received from the same physical receptor on a spectrophotometer, however the incident light came from multiple angles.

When using spectral reflectance data, the calculation may be made individually for each wavelength. In various embodiments, statistics, such as mean, median, and sum may be used to create a singular value out of multiple wavelength calculated Kepler's laws of planetary motion values. In various embodiments, an individual specific wavelength or wavelengths may be compared using Kepler's laws of planetary motion analysis. Such embodiments permit the study of the wavelength or wavelengths of maximum reflectance, and potentially secondary maximum reflectance, where a majority of color and/or texture is visibly perceived. In various embodiments, an analysis of shifting maximum reflectances by wavelength may also be completed using Kepler's laws of planetary motion analysis.

In various embodiments, at step 16 of FIG. 1 the calculated Kepler's laws of planetary motion values from the colorimetric or spectral reflectance data may further be empirically correlated to known characteristics in order to identify textures, primary flake types, or other appearance information in complex coating mixtures. To employ an empirical method, the Kepler's laws of planetary motion data points (eccentricity, semi-latus rectum, angular velocity, mean motion, areal velocity, orbital period, semi-major axis, etc.) are calculated for an empirical dataset and all desired combinations of angles, representative of the expected mixtures and colors that need to be or are desired to be handled in everyday situations. The empirical data set may be used to create a predictive correlation: y=f(x), where y represents the desired characteristic for identification or a qualitative question regarding the target coating, and f(x) is some function of x's, where x is one or multiple variables using the Kepler's laws of planetary motion values calculated from a specific set or multiple sets of angular considerations. In various embodiments, certain situations, it may be desirable to limit the angular comparison sets to the specific that are most feature-defining for the particular characteristic that is being identified. The resulting function may be linear or non-linear as defined by the empirical data set.

Figure 5:
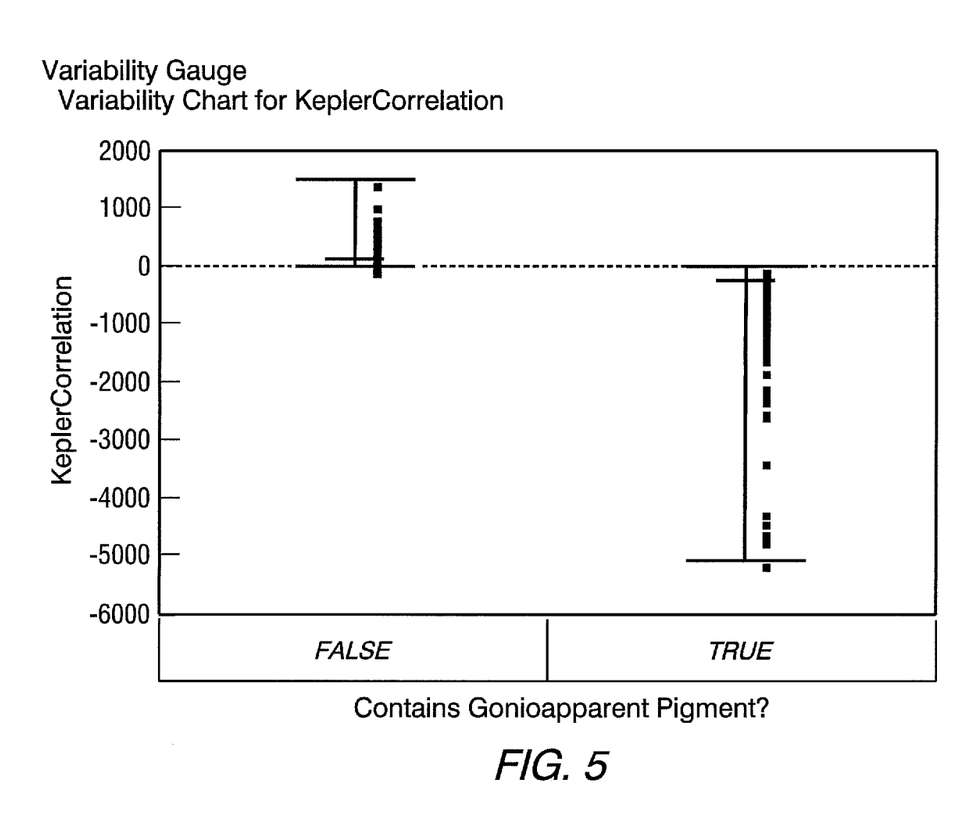
FIG. 5 illustrates an example of the use of Kepler's laws of planetary motion data using a specific combination of angles to predict whether a target coating contains a gonioapparent effect.

FIG. 5 illustrates an example of the use of Kepler's laws of planetary motion data using a specific combination of angles to predict whether a target coating contains a gonio-apparent effect. There is a clear division where the correlation using Kepler's laws of planetary motion data is roughly at or above zero, indicating a lack of gonioapparent effect, while values below zero indicate the use of a gonioapparent effect.

Once an empirical correlation has been determined, at step 18 of FIG. 1 it may be used to derive the predicted value for the target coating. In various embodiments, this is achieved by using the target coating's values for the x's (eccentricity, semi-latus rectum, angular velocity, mean motion, areal velocity, orbital period, semi-major axis, etc.) and calculating the result for y (the texture effect). While examples here have been given for the content of a gonio-apparent pigment, in various embodiments the methodology may be as specific as which gonioapparent pigment at which size flake of that pigment is present by iteratively choosing the most important single angles or combinations of angles for the Kepler's laws of planetary motion calculations and empirical correlations. The choice of angular comparisons and to what level they are combined may be used to create the best possible empirical correlation. In various embodiments, the empirical correlations may also be slightly improved by including other "non-Kepler" information, for example singular angle colorimetric data.

In various embodiments, the quality of the overall "map," or "fingerprint," approach and the quality of the empirical correlation approach may be dependent upon the quality of the input data. The quality of the input data may be dependent upon the quality of the instrumentation and the quality of the data set used to create a set of knowns for the overall map or the empirical correlation. While any quality of data from an instrument or an empirical data set will result in an answer, the answer may be improved with the use of a high quality instrument and a widely varied, high quality empirical data set.

The entire set of calculations described herein may be used in conjunction with a processor in order to facilitate the choice of specific angle combination as well as accommodate the volume of calculations required in order to derive and then use an empirical correlation using the Kepler's laws of planetary motion data.

Figure 6:
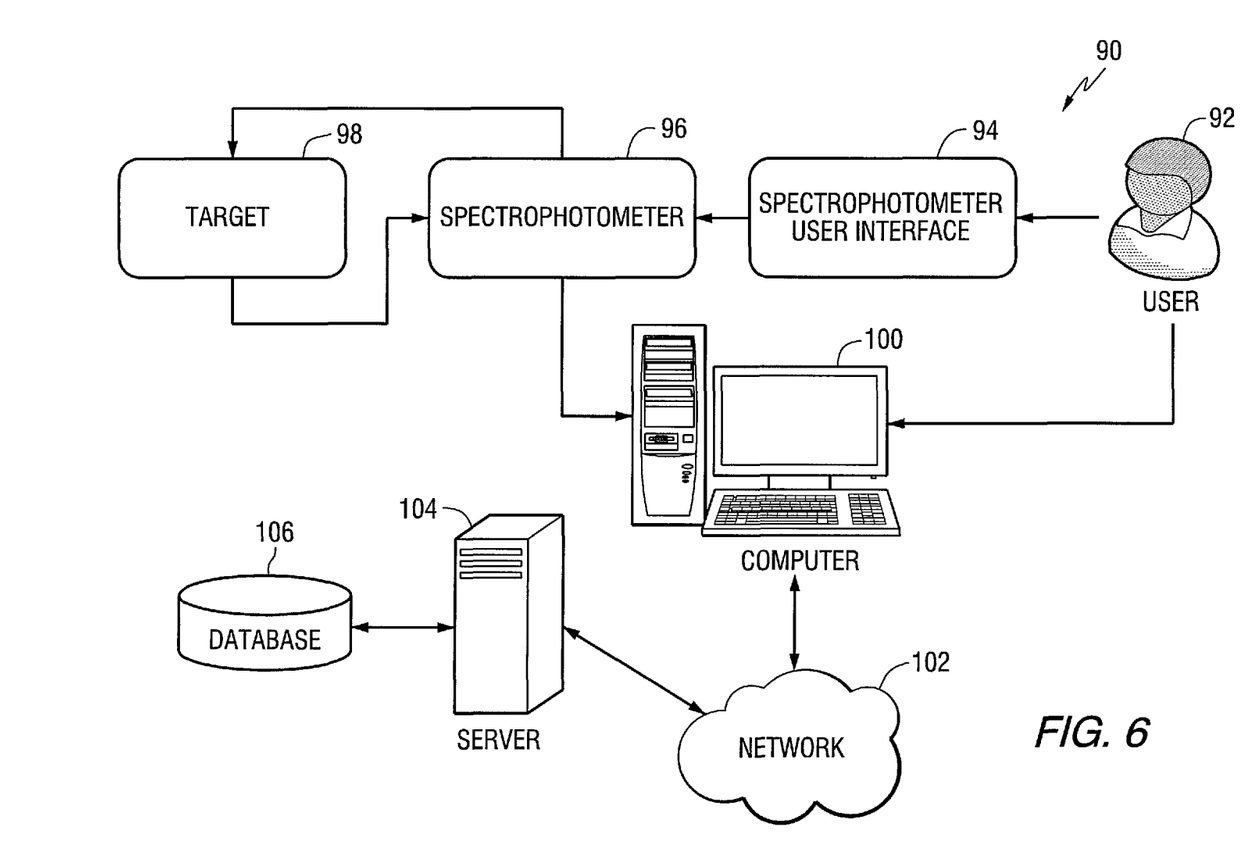
FIG. 6 illustrates an embodiment of a system which may be used to identify physical property attributes of a coating mixture of a target sample.

FIG. 6 illustrates an embodiment of a system 90 which may be used to identify physical property attributes of a coating mixture of a target sample. A user 92 may utilize a user interface 94, such as a graphical user interface, to operate a spectrophotometer 96 to measure the properties of a target sample 98. The data from the spectrophotometer 96 may be transferred to a computer 100, such as a personal computer, a mobile device, or any type of processor. The computer 100 may be in communication, via a network 102, with a server 104. The network 102 may be any type of network, such as the Internet, a local area network, an intranet, or a wireless network. The server 104 is in communication with a database 106 that may store the data and information that is used by the methods of embodiments of the present invention for comparison purposes. In various embodiments the database 106 may be utilized in, for example, a client server environment or in, for example, a web based environment such as a cloud computing environment. Various steps of the methods of embodiments of the present invention may be performed by the computer 100 and/or the server 106.

It will be readily appreciated by those skilled in the art that modifications may be made to the invention without departing from the concepts disclosed in the forgoing description. Such modifications are to be considered as included within the following claims unless the claims, by their language, expressly state otherwise. Accordingly, the particular embodiments described in detail herein are illustrative only and are not limiting to the scope of the invention which is to be given the full breadth of the appended claims and any and all equivalents thereof.

In another aspect, the invention may be implemented as a non-transitory computer readable medium containing software for causing a computer or computer system to perform the method described above. The software can include various modules that are used to enable a processor and a user interface to perform the methods described herein.

It will be readily appreciated by those skilled in the art that modifications may be made to the invention without departing from the concepts disclosed in the forgoing description. Accordingly, the particular embodiments described in detail herein are illustrative only and are not limiting to the scope of the invention.

What is claimed is:

1. A computer implemented method for efficiently identifying compositions of a target coating using planetary motion equations and limited data measurements, comprising:

generating through a computer system a hemispherical fingerprint for each pigment or texture of a plurality of pigments or textures in an empirical data set, wherein: (i) each hemispherical fingerprint comprises a plurality of elliptical shapes defined by measured data taken from a plurality of angles by a first spectrophotometer; and (ii) each elliptical shape comprises a mixture of plot points comprising the measured data, and virtual color response data generated using Kepler's laws of planetary motion in connection with the measured data;

obtaining, from a second spectrophotometer, reflectance data from a target coating using the same or fewer than the plurality of angles measured for the empirical data set;

calculating, using the processor, virtual color response data for the target coating using one of at least one Kepler's laws of planetary motion equation and at least one derivation of at least one Kepler's laws of planetary motion equation, thereby generating one or more virtual ellipses for the target coating;

comparing the virtual ellipses calculated for the target coating to each ellipse in the empirical data set to identify a matched pigment or texture, wherein each virtual ellipse and each ellipse of the empirical data set comprises data corresponding to one or more eccentricity values, semi-latus rectum values, angular velocity values, mean motion values, areal velocity values, orbital period values, and major axis values; and generating, using the processor, a coating formulation that is the same or substantially similar in appearance to the target coating using the matched pigment or texture.

2. The method of claim 1, wherein generating a coating formulation comprises correlating the virtual color response data to a plurality of known data and predicting at least one texture feature of the target coating based on the correlating.

3. The method of claim 2, wherein correlating the virtual color response data to a plurality of known data comprises empirically correlating the virtual color response data to a plurality of known data.

4. The method of claim 2, wherein predicting at least one texture feature of the target coating based on the correlating comprises predicting, using at least one empirical calculation, at least one texture feature of the target coating based on the correlating.

5. A computer system, comprising:

a database; and a processor in communication with the database and programmed to efficiently identify compositions of a target coating using planetary motion equations and limited data measurements by executing the following:

generate through a computer system a hemispherical fingerprint for each pigment or texture of a plurality of pigments or textures in an empirical data set, wherein: (i) each hemispherical fingerprint comprises a plurality of elliptical shapes, each elliptical shape in the plurality being defined by measured data taken from a plurality of angles by a first spectrophotometer; and (ii) each elliptical shape comprises a mixture of plot points comprising the measured data, and virtual color response data generated using Kepler's laws of planetary motion in connection with the measured data;

obtain from a second spectrophotometer, reflectance data from a target coating using the same or fewer than the plurality of angles measured for the empirical data set;

calculate, using the processor, virtual color response data using one of at least one Kepler's laws of planetary motion equation and at least one derivation of at least one Kepler's laws of planetary motion equation, thereby generating one or more virtual ellipses for the target coating;

compare the virtual ellipses calculated for the target coating to each ellipse in the empirical data set to identify a matched pigment or texture, wherein each virtual ellipse and each ellipse of the empirical data set comprises data corresponding to one or more eccentricity values, semi-latus rectum values, angular velocity values, mean motion values, areal velocity values, orbital period values, and major axis values; and generate using the processor, a coating formulation that is the same or substantially similar in appearance to the target coating using the matched pigment or texture.

6. The system of claim 5, wherein the first and second spectrophotometers are communication with the processor.

7. The system of claim 5, wherein the processor is further configured to:

identify a first and second gonioapparent pigment and a corresponding flake size thereof; and select a first subset of angles of the obtained reflectance data that correlate with the first gonioapparent pigment and corresponding flake size; and select a second subset of angles of the obtained reflectance data that correlate with the second gonioapparent pigment and corresponding flake size;

wherein the first subset of angles is different from the second subset of angles.

8. The system of claim 7, wherein generating a coating formulation comprises correlating the virtual color response data to a plurality of known data and predicting at least one texture feature of the target coating based on the correlating.

9. The system of claim 8, wherein correlating the virtual color response data to a plurality of known data comprises empirically correlating the virtual color response data to a plurality of known data.

10. The system of claim 8, wherein the predicting at least one texture feature of the target coating based on the correlating comprises predicting, using at least one empirical calculation, at least one texture feature of the target coating based on the correlating.

11. A non-transitory computer readable medium including computer-executable instructions that, when executed on a computer system, cause a processor of the computer system to:

generate a hemispherical fingerprint for each pigment or texture of a plurality of pigments or textures in an empirical data set, wherein: (i) each hemispherical fingerprint comprises a plurality of elliptical shapes, each elliptical shape in the plurality being defined by measured data taken from a plurality of angles by a first spectrophotometer; and (ii) each elliptical shape comprises a mixture of plot points comprising the measured data, and virtual color response data generated using Kepler's laws of planetary motion in connection with the measured data obtain reflectance data from a target coating using the same or fewer than the plurality of angles measured for the empirical data set;

calculate virtual color response data using one of at least one Kepler's laws of planetary motion equation and at least one derivation of at least one Kepler's laws of planetary motion equation, thereby generating one or more virtual ellipses for the target coating;

compare the virtual ellipses calculated for the target coating to each ellipse in the empirical data set to identify a matched pigment or texture, wherein each virtual ellipse and each ellipse of the empirical data set comprises data corresponding to one or more eccentricity values, semi-latus rectum values, angular velocity values, mean motion values, areal velocity values, orbital period values, and major axis values; and generate a coating formulation that is the same or substantially similar in appearance to the target coating using the matched pigment or texture.

12. The computer readable medium as recited in claim 11, further comprising instructions that cause the processor to:

identify a first and second gonioapparent pigment and a corresponding flake size thereof; and select a first subset of angles of the obtained reflectance data that correlate with the first gonioapparent pigment and corresponding flake size; and select a second subset of angles of the obtained reflectance data that correlate with the second gonioapparent pigment and corresponding flake size;

wherein the first subset of angles is different from the second subset of angles.

13. The computer readable medium as recited in claim 12, further comprising instructions that cause the processor to:

correlate each of the first and second subsets of angles with colorimetric data.

14. The computer readable medium as recited in claim 11, wherein the instructions further cause the processor to:

interpolate one or more angular responses for the target coating, wherein the one or more interpolated responses comprise values that are not physically captured by a spectrophotometer;

wherein the matched pigment or texture comprises a match between the interpolated one or more angular responses and the empirical data set.

15. The computer readable medium as recited in claim 1, further comprising:

identifying a first and second gonioapparent pigment and a corresponding flake size thereof; and selecting a first subset of angles of the obtained reflectance data that correlate with the first gonioapparent pigment and corresponding flake size; and selecting a second subset of angles of the obtained reflectance data that correlate with the second gonioapparent pigment and corresponding flake size;

wherein the first subset of angles is different from the second subset of angles.

16. The computer readable medium as recited in claim 15, further comprising:

correlating each of the first and second subsets of angles with colorimetric data.

17. The computer readable medium as recited in claim 1, further comprising:

interpolating one or more angular responses for the target coating, wherein the one or more interpolated responses comprise values that are not physically captured by a spectrophotometer; and wherein the matched pigment or texture comprises a match between the interpolated one or more angular responses and the empirical data set.

18. The system of claim 5, wherein the processor is further configured to:
identify a first and second gonioapparent pigment and a corresponding flake size thereof; and
select a first subset of angles of the obtained reflectance data that correlate with the first gonioapparent pigment and corresponding flake size; and
select a second subset of angles of the obtained reflectance data that correlate with the second gonioapparent pigment and corresponding flake size;
wherein the first subset of angles is different from the second subset of angles.

19. The system of claim 18, wherein the processor is further configured to:
correlate each of the first and second subsets of angles with colorimetric data.

20. The system of claim 5, wherein the processor is further configured to:
interpolate one or more angular responses for the target coating, wherein the one or more interpolated responses comprise values that are not physically captured by a spectrophotometer; and
wherein the matched pigment or texture comprises a match between the interpolated one or more angular responses and the empirical data set.

* * * * *